(12) United States Patent
Acton

(10) Patent No.: US 9,272,118 B1
(45) Date of Patent: Mar. 1, 2016

(54) METHODS FOR TREATING BRAIN MALFUNCTIONS

(71) Applicant: George Acton, Shreveport, LA (US)

(72) Inventor: George Acton, Shreveport, LA (US)

( * ) Notice: Subject to any disclaimer, the term of this patent is extended or adjusted under 35 U.S.C. 154(b) by 197 days.

(21) Appl. No.: 13/784,193

(22) Filed: Mar. 4, 2013

(51) Int. Cl.
*A61M 21/00* (2006.01)
*A61M 21/02* (2006.01)

(52) U.S. Cl.
CPC ..................... *A61M 21/02* (2013.01)

(58) Field of Classification Search
CPC ............... A61M 21/00; A61M 21/02; A61M 2021/0005; A61M 2021/0027; A61M 2021/0044
USPC ...................................... 600/26–28
See application file for complete search history.

(56) References Cited

U.S. PATENT DOCUMENTS

| 2006/0030907 A1* | 2/2006 | McNew | 607/88 |
| 2012/0150545 A1* | 6/2012 | Simon | 704/270 |
| 2013/0172663 A1* | 7/2013 | Leonard | 600/27 |
| 2013/0331444 A1* | 12/2013 | Sun et al. | 514/450 |

OTHER PUBLICATIONS

Kang et al., "Amyloid-Beta Dynamics Are Regulated by Orexin and the Sleep-Wake Cycle," Science, Nov. 13, 2009, vol. 326, p. 1005-1007.*
Kohdabashi, et al., "Evaluating the Entrainment of Alpha Rythym During Photic Stimulation in Control Subjects and Patients with Alzheimer's Disease", Int'l Journal of Bioelectromagnatism, 7(46):177-180 (2005).

* cited by examiner

*Primary Examiner* — Charles A Marmor, II
*Assistant Examiner* — Thaddeus Cox
(74) *Attorney, Agent, or Firm* — David P. Lentini

(57) ABSTRACT

Methods of treating a brain malfunction include obtaining a subject diagnosed with a brain malfunction and reducing EEG frequency of brainwaves in the subject by applying at least one EEG-slowing stimulus to the subject, whereby production of beta amyloid protein in the brain of the subject is reduced and progression of the brain malfunction is halted or slowed.

14 Claims, 2 Drawing Sheets

METHODS FOR TREATING BRAIN MALFUNCTIONS

CROSS-REFERENCE TO RELATED APPLICATIONS

This application claims the benefit of U.S. provisional application No. 61/606,052, filed Mar. 2, 2012 and entitled A METHOD FOR TREATING BRAIN MALFUNCTIONS THROUGH ENTRAINMENT, which provisional application is incorporated by reference herein in its entirety.

FIELD

Illustrative embodiments of the disclosure generally relate to methods for treating brain malfunctions related to excessive levels of beta amyloid protein. More particularly, illustrative embodiments of the disclosure relate to methods for treating brain malfunctions which are caused or exacerbated by excessive levels of beta amyloid protein by reducing the levels of beta amyloid protein in brain tissue through entrainment, binaural beats and/or neurofeedback.

BACKGROUND

Several brain malfunctions or diseases are caused or exacerbated by high levels of beta amyloid protein. Examples of these brain malfunctions include Alzheimer's disease, Down Syndrome and Fragile X Syndrome. Alzheimer's disease (AD) is the most common cause of age-related dementia, affecting over 5 million individuals in the US alone. Death as a result of AD occurs, on average, nine years after diagnosis with a devastating effect on quality of life and burden on caregivers throughout the course of the disease.

The first brain structures damaged in AD are those serving short term memory (hippocampus and neighboring temporal lobe). The disease then spreads to the parts of the temporal, parietal and frontal lobes which function in memory, judgment and cognition. Parts of the brain that are specialized for sensory and motor functions are relatively spared, especially the occipital lobe (visual system). The regions of the brain which have been characterized as most vulnerable to AD are known as the "default mode network" (DMN), a system in the cerebral cortex that becomes active when attention isn't focused on a specific mental task. One estimate is that people spend 50% of waking time in the mental activities mediated by the DMN. The DMN is integral in recalling past events, anticipating future events, providing the sense of self and the intuitive grasp of the emotions of others, and making future plans. The DMN has the highest metabolic rate of cortical areas, which likely accounts for its vulnerability in AD. Compounding the problem is that the DMN is spread widely over the cerebral hemispheres, requiring neurons with long axons to maintain coordination. AD causes the DMN to become even more active, possibly in an attempt to compensate for lost neurons.

Conventional therapies for treating AD focus on controlling symptoms rather than halting or slowing progression of the disease. In practice, the benefits of presently-available treatment strategies last typically only up to about 2 years. Drugs which are being tested for treatment of AD may not be available for years. In the meantime, the demand for a course of therapy that halts or slows progression of the disease is enormous.

The currently accepted theory regarding the cause of AD is that the disease results from an excess buildup of a normal protein known as beta amyloid in the brain. Beta amyloid is normally discharged into synapses between neurons and transiently binds to neurotransmitter receptors at nerve cell membranes, after which it is cleared from the synapse by one of several mechanisms, primarily by transport away from the brain through the bloodstream.

There is ample evidence that excess beta amyloid results from diminished clearance of the protein from the brain even when normal protein production levels prevail. The capacity and effectiveness of clearance declines with age; therefore, AD can be viewed as an exaggeration of the effects of normal aging. Most of the insufficiently-cleared beta amyloid protein aggregates outside of cells in structures known as plaques that are visible under a light microscope. At the stage of AD when the loss of neurons begins, the plaques are close to maximal size. Chemical analysis shows up to 1000 times the normal level of beta amyloid in brain tissue from AD patients, and this beta amyloid exists almost entirely in the form of plaque. The toxic form of beta amyloid is one of the small aggregates (dimers, oligomers and fibrils) which reach toxic levels only at a critical concentration. A small decrease in the production of beta amyloid in brain tissue may potentially slow or halt the course of the disease.

Accordingly, methods for treating brain malfunctions which are caused or exacerbated by excessive levels of beta amyloid protein by reducing the production of the beta amyloid in brain tissue through entrainment, binaural beats and/or neurofeedback may be effective in the treatment of AD and other related conditions.

SUMMARY

Illustrative embodiments of the disclosure are generally directed to methods of treating a brain malfunction which are caused or exacerbated by excessive levels of beta amyloid protein in the brain. The methods may include obtaining a subject diagnosed with a brain malfunction and reducing EEG frequency of brainwaves in the subject by applying at least one EEG-lowering stimulus to the subject, whereby production of beta amyloid protein in the brain of the subject is reduced and progression of the brain malfunction is halted or slowed.

BRIEF DESCRIPTION OF THE DRAWINGS

Illustrative embodiments of the disclosure will now be described, by way of example, with reference to the accompanying drawings, in which.

DETAILED DESCRIPTION

Figure 1:
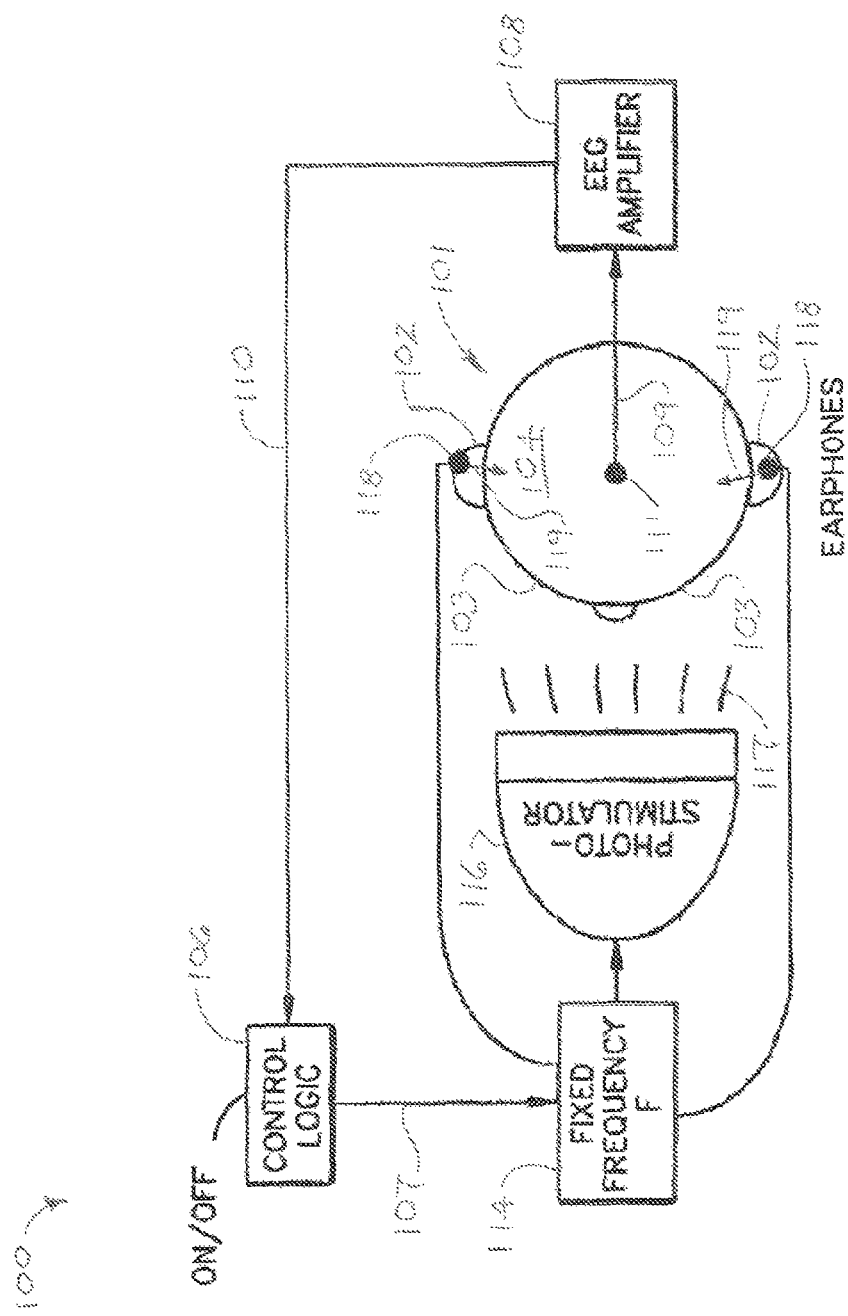
FIG. 1 is a schematic diagram of an exemplary entrainment induction system in implementation of an illustrative embodiment of the methods for treating brain malfunctions.

The following detailed description is merely exemplary in nature and is not intended to limit the described embodiments or the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable users skilled in the art to practice the disclosure and are not intended to limit the scope of the claims. Moreover, the illustrative embodiments described herein are not exhaustive and embodiments or implementations other than those which are described herein and which fall within the scope of the appended claims are possible. Furthermore, there is no intention to be bound by any expressed or implied theory presented in the preceding technical field, background, brief summary or the following detailed description.

Illustrative embodiments of the disclosure are directed to methods for treating brain malfunctions which are caused or exacerbated by excessive levels of beta amyloid protein (Ab) in neural tissues. The methods may include lowering the EEG (electroencephalogram) frequency of brainwaves which characterize the waking state, to reduce neural activity and metabolism. Reduction of neural activity and metabolism may, in turn, lower the rate of production of Ab in neural tissues and prevent or reduce formation of amyloid plaques in the brain, halting or at least slowing progression of the brain malfunction. Non-limiting examples of brain malfunctions which can be treated using the methods include Alzheimer's Disease, Down Syndrome and Fragile X Syndrome.

Dramatic changes in the EEG frequency spectrum are associated with a decline in Ab production during sleep. Most of sleep consists of "slow wave sleep", in which about 75% of the brainwave power or EEG power spectrum is in the low frequency range (delta, 0-5 Hz and theta, 5-7 Hz). In the deeper stages of sleep, delta may account for about 60% of the brainwaves. During waking, about 50% of the brainwave power or EEG power spectrum is in the higher frequency ranges (alpha, 8-12 Hz; beta, 13-30 Hz; and gamma, over 30 Hz). In some embodiments of the methods, reducing the beta frequency of brainwaves in the waking state may be sufficient to reduce Ab production, in which case reduction of the brainwaves to alpha frequency may be protective. In some embodiments, reduction of the brainwaves to lower frequencies (theta, delta) may suppress both beta and alpha frequencies, which may be beneficial for reducing Ab production.

The illustrative methods of the disclosure may halt or slow progression of brain malfunction in patients by reducing the production of Ab in the brain tissue of the subjects. Reduction in the production of Ab in the brain tissue of the subjects may be accomplished by reducing the EEG frequency of brainwaves in the subject. Reduction of the EEG frequency of the brainwaves in the subject may be accomplished by regularly subjecting the patient to at least one stimulus which lowers the EEG frequency of the patient's brainwaves. The EEG frequency-lowering stimulus may include at least one entrainment stimulus (visual and/or auditory), binaural beats, neurofeedback, tactile stimuli, kinesthetic stimuli, somatic electrical stimuli, transcranial electrical stimuli, transcranial magnetic stimuli or any combination thereof.

The methods may be effective in reducing Ab production in brain structures which tend to be the most vulnerable to AD, particularly those serving short term memory (hippocampus and the neighboring temporal lobe) as well as those which function in memory, judgment and cognition (parts of the temporal, parietal and frontal lobes). The methods may be particularly effective in treatment of the "default mode network" (DMN), a system in the cerebral cortex that becomes active when attention isn't focused on a specific mental task and which is particularly vulnerable to AD. The subsystems of the DMN may include part of the medial temporal lobe which is involved in memory, part of the medial prefrontal cortex (emotional intuition) and the posterior cingulate cortex (integration), along with the adjacent ventral precuneus and the medial, lateral and inferior parietal cortex.

Entrainment is a process in which the electrical activity of the brain settles into brainwaves of the same frequency when a repetitive stimulus is presented to a subject. Brainwave frequencies which are induced by entrainment may spread from the area which is stimulated to involve other parts of the cortex.

Binaural beats are perceived sounds produced within the nervous system. When pure tones of slightly different frequencies are presented separately to each ear, the subject has the sensation of a sound at the frequency representing the difference of the input frequencies. Binaural beats may have effects on the EEG frequency spectrum which may be beneficial in lowering Ab levels.

Neurofeedback involves monitoring a physiologic variable not under conscious control and signaling to the subject when the desired change is present, usually with an audible tone. It can be used with EEG frequencies, muscle tone, skin conductance, heart rate and pain perception.

Illustrative embodiments of the disclosure may include obtaining a subject diagnosed with a brain malfunction which is caused or exacerbated by excessive levels of beta amyloid protein. A stimulus protocol may be formulated. The stimulus protocol may include applying at least one EEG frequency-lowering stimulus to a subject. The EEG frequency-lowering stimulus may include at least one entrainment stimulus (visual and/or auditory), binaural beats, neurofeedback, tactile stimuli, kinesthetic stimuli, somatic electrical stimuli, transcranial electrical stimuli, transcranial magnetic stimuli or any combination thereof. The stimulus may cause a reduction in the EEG frequency of brainwaves in the subject. The reduction in the EEG frequency may cause a reduction in Ab production in the subject. The reduction in AB production in the subject may result in a halting or at least slowing of the progression of the brain malfunction in the subject. The progress of the brain malfunction may be monitored throughout the treatment regimen.

Referring initially to FIG. 1 of the drawings, a schematic diagram of an exemplary entrainment induction system which is suitable, for inducing entrainment in a subject in implementation of an illustrative embodiment of the methods for treating brain malfunctions, hereinafter system, is generally indicated by reference numeral 100. The system 100 is adapted to apply at least one EEG frequency-lowering stimulus to a subject 101. In some embodiments of the methods, the system 100 may include any of a variety of conventional sound and light machines which are suitable for the purpose of lowering the EEG brainwave frequency of the subject 101 through entrainment, binaural beats, neurofeedback or any combination thereof according to the knowledge of those skilled in the art. Generally, the system 100 may include an EEG amplifier 108 which is adapted to detect brainwaves through sensors 111 placed on the scalp 104 of the subject 101 and convert the detected brainwaves into an EEG spectrum. A control logic 106 interfaces with the EEG amplifier 108. The control logic 106 is adapted to receive EEG frequency readings 110 from the EEG amplifier 108.

A stimulus controller 114 interfaces with the control logic 106. A photo-stimulator 116 may interface with the stimulus controller 114. The photo-stimulator 116 may be adapted to emit photo-stimuli 117 into the eyes 103 of the subject 101. In some embodiments, the photo-stimulator 116 may include a computer monitor or any other device which is capable of emitting photo-stimuli 117 of a selected type, intensity, frequency and duration. In other embodiments, the photo-stimulator 116 may include photo-stimulating goggles which are known by those skilled in the art. An example of photo-stimulating goggles which may be suitable as the photo-stimulator 116 are described in U.S. Pat. No. 5,709,645, which is incorporated by reference herein in entirety. Photo-stimulating goggles may include LEDs which emit the photic stimulus 117. A pair of earphones 118 may interface with the stimulus controller 114. The earphones 118 may be adapted to emit auditory stimuli 119 of a selected type, intensity, frequency and duration into the ears 102 of the subject 101.

The control logic 106, via the stimulus controller 114, may be adapted to control parameters such as the type, intensity and frequency of the photo-stimuli 117 emitted by the photo-stimulator 116 and the auditory stimuli 119 emitted by the earphones 118, as well as any phase differences and/or time differences between the photo-stimuli 117 and the auditory stimuli 119 which may be necessary or conducive to induce brainwaves of a selected EEG frequency in the subject 101. The photic stimulus and auditory stimulus parameters which are necessary to induce brainwaves having various selected EEG frequencies are known by those skilled in the art and need not be discussed in detail herein. In some embodiments, the control logic 106 may be part of a desktop or laptop computer or tablet or other external data processing device. The control logic 106 may include memory which records a log of the times and effectiveness of treatment. This expedient may be useful for self-evaluation and review of stimulus protocols and treatment results by attending physicians or other professionals.

In some embodiments, the stimulus controller 114 may be adapted to receive from the control logic 106 input which is indicative of the frequency of the EEG frequency readings 110 from the subject 101. The stimulus controller 114 may be adapted to adjust the parameters of the stimuli emitted by the photo-stimulator 116 and/or the earphones 118 to lower the brainwave frequency of the subject 101 to a selected level below that which is indicated by the EEG frequency readings 110. For example, in some embodiments of the methods, the control logic 106 may use the EEG frequency readings 110 to modify entraining photo-stimuli 117 and/or entraining auditory stimuli 119 by setting either or both stimuli lower than the current frequency range which is indicated by the EEG frequency readings 110. The EEG frequency readings 110 can also be used to deliver feedback about whether the target EEG frequencies of the subject 101 are occurring via neurofeedback. In some embodiments, neurofeedback may be administered without sensory stimulation via the photo-stimulator 116 and/or the earphones 118.

Figure 2:
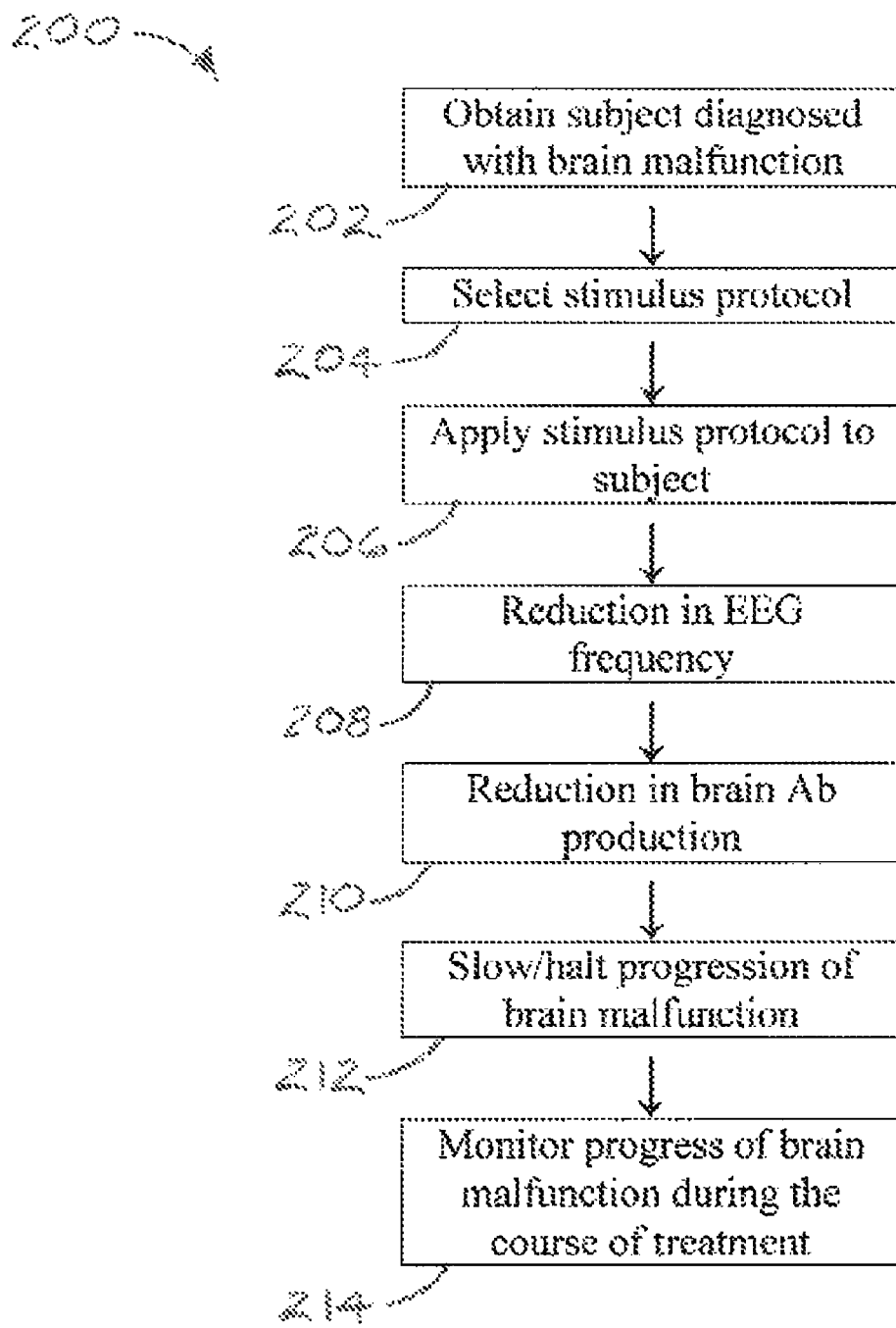
FIG. 2 is a flow diagram of illustrative embodiments of the methods for treating brain malfunctions.

Referring next to FIGS. 1 and 2 of the drawings, a flow diagram 200 of an illustrative embodiment of the methods for treating brain malfunctions is illustrated. In block 202, a subject which has been diagnosed with a brain malfunction caused or exacerbated by excessive levels of beta amyloid protein (Ab) in the brain is obtained. Non-limiting examples of brain malfunctions which may be caused or exacerbated by excessive levels of Ab and which are amenable to treatment using the methods of the disclosure include Alzheimer's Disease, Down Syndrome and Fragile X Syndrome.

In block 204, a stimulus protocol may be selected. The stimulus protocol may include parameters (type, frequency, intensity, timing, duration, phase, etc.) of the photo-stimuli 117 which are emitted from the photo-stimulator 116 and of the auditory stimuli 119 which are emitted from the earphones 118 of the system 100, binaural beats, neurofeedback, tactile stimuli, kinesthetic stimuli, somatic electrical stimuli, transcranial electrical stimuli, transcranial magnetic stimuli or any combination thereof. In some embodiments, the stimulus protocol may be selected to reduce or minimize brainwaves having beta (13-30 Hz) and gamma (30+ Hz) EEG frequencies. Brainwave frequencies in the delta (<5 Hz) and/or theta (5-7 Hz) ranges may be selected in some applications to eliminate or at least minimize Ab synthesis. The stimulus protocol may be based on previous data from entrainment sessions of the same or other subjects 101 or from the response of the subject 101 in real time using the EEG frequency readings 110 from the EEG amplifier 108.

In embodiments of the methods in which the stimulus protocol includes entrainment, the phases of the photo-stimuli 117 and the auditory stimuli 119 may be varied over the course of a treatment session to induce beginning frequencies that are amenable to entrainment (alpha, 8-12 Hz) and then falling to the preferred lower frequencies (theta, 5-7 Hz and/or delta, <5 Hz). Visual and auditory pathways have different delays on the way to the cerebral cortex. Therefore, the most effective entrainment may result from synchronizing the photo-stimuli 117 and the auditory stimuli 119 to mutually reinforce at the cortical level, and this may depend on absolute time rather than phase. The efficiency of entrainment may be monitored via the EEG amplifier 108 and the control logic 106 of the system 100. Careful adjustment of the time delay between the photo-stimuli 117 and the auditory stimuli 119 may optimize entrainment. In some embodiments, the auditory stimuli 119 may be isochronic and in-phase with the photo-stimuli 117. The photo-stimuli 117 may be a smoothed square wave to reduce harmonics. In some entrainment embodiments, binaural beats may be used in addition to or instead of isochronic auditory stimuli 119.

In block 206, the stimulus protocol may be carried out on the subject 101 in daily treatment sessions to maintain the halted or suppressed production of Ab. Each treatment session may include maintaining the reduced EEG frequency of the subject 101 for at least about 1 hour and typically about 2-4 hours or more. In some embodiments, the length of the treatment sessions may be increased to accord with the falling clearance of Ab. In block 208, the stimulus protocol results in a reduction in EEG frequency of brainwaves in the subject 101. The reduction in EEG frequency of the brainwaves in the subject 101 reduces Ab production in the brain of the subject 101 (block 210), slowing or halting progression of the brain malfunction (block 212) over time.

In block 214, the progress of the brain malfunction in the subject 101 may be monitored throughout treatment to determine the efficacy of the treatment. Testing for specific chemical changes may be carried out using a blood test, but may require an invasive procedure involving a lumbar puncture with placement of a small drainage tube (cannula) in the spinal canal for several hours. Other methods of monitoring the progress of the brain malfunction in the subject 101 may include periodic fMRI (functional Magnetic Resonance Imaging) of affected areas. The methods of the disclosure may be effective in halting progression of brain malfunctions which are caused or exacerbated by excessive brain levels of amyloid beta protein for several years around the time of clinical onset until a cure (e.g., monoclonal antibody therapy) for the malfunction is found.

While the illustrative embodiments of the disclosure have been described above, it will be recognized and understood that various modifications can be made to the embodiments and the appended claims are intended to cover all such modifications which may fall within the spirit and scope of the disclosure.

What is claimed is:
1. A method of treating a brain malfunction related to accumulation of beta amyloid protein in a subject, comprising: exposing said subject to at least one photic or aural stimulus for at least about one hour to substantially suppress or substantially eliminate beta and gamma EEG frequencies of said subject compared to the beta and gamma EEG fre- quencies of said subject without said exposure; and reducing, using said exposure, the production of beta amyloid protein in the brain of said subject.

2. The method of claim 1 wherein said subject has been diagnosed with Alzheimer's Disease.

3. The method of claim 1 wherein said subject has been diagnosed with Down Syndrome.

4. The method of claim 1, further comprising substantially suppressing or substantially eliminating alpha EEG frequencies.

5. The method of claim 1, further comprising enhancing theta EEG frequencies.

6. The method of claim 1, further comprising enhancing delta EEG frequencies.

7. The method of claim 1 wherein said stimulus includes an aural stimulus comprising binaural beats.

8. A method of treating a brain malfunction related to accumulation of beta amyloid protein in a subject, comprising:
 selecting a treatment protocol including exposing said subject to at least one aural or photic stimulus for at least about one hour to induce entrainment of electrical activity in the brain of said subject;
 applying said treatment protocol to said subject; and
 substantially reducing or eliminating the beta and gamma of EEG frequencies compared to the EEG frequencies of said subject without said exposure; and reducing, using said exposure, the production of beta amyloid protein in the brain of the subject.

9. The method of claim 8 wherein said subject has been diagnosed with Alzheimer's Disease.

10. The method of claim 8 wherein said subject has been diagnosed with Down Syndrome.

11. The method of claim 8, further comprising substantially suppressing or substantially eliminating alpha EEG frequencies.

12. The method of claim 8, further comprising enhancing theta EEG frequencies.

13. The method of claim 8, further comprising enhancing delta EEG frequencies.

14. The method of claim 8 wherein said stimulus includes an aural stimulus comprising binaural beats.

* * * * *